(12) United States Patent
Walsh et al.

(10) Patent No.: US 8,068,914 B1
(45) Date of Patent: Nov. 29, 2011

(54) SPEECH PROCESSOR CASES

(75) Inventors: Thomas Patrick Walsh, Valencia, CA (US); Carla Mann Woods, Beverly Hills, CA (US); Richard C. Ross, Westlake Village, CA (US); Rankiri Tissa Karunasiri, Castaic, CA (US); Anthony K. Arnold, Valencia, CA (US)

(73) Assignee: Advanced Bionics, LLC, Valencia, CA (US)

( * ) Notice: Subject to any disclaimer, the term of this patent is extended or adjusted under 35 U.S.C. 154(b) by 373 days.

(21) Appl. No.: 11/121,756

(22) Filed: May 4, 2005

Related U.S. Application Data

(60) Provisional application No. 60/568,450, filed on May 5, 2004.

(51) Int. Cl.
*A61N 1/375* (2006.01)
(52) U.S. Cl. ............... 607/55; 607/136; 607/36; 607/56; 607/57; 607/137
(58) Field of Classification Search ............... 607/55–57, 607/36–37, 48, 60, 115, 136–139
See application file for complete search history.

(56) References Cited

U.S. PATENT DOCUMENTS

| | | | | |
|---|---|---|---|---|
| 1,422,877 | A * | 7/1922 | Maxfield | 381/23.1 |
| 4,248,237 | A | 2/1981 | Kenny | |
| 4,347,956 | A | 9/1982 | Berger | |
| 4,419,995 | A * | 12/1983 | Hochmair et al. | 607/57 |
| 4,456,797 | A | 6/1984 | Olsen | |
| 4,532,930 | A * | 8/1985 | Crosby et al. | 607/57 |
| 4,545,381 | A * | 10/1985 | Bournay et al. | 607/10 |
| 4,562,590 | A | 12/1985 | DeLage | |
| 4,584,718 | A | 4/1986 | Fuller | |
| 4,682,363 | A | 7/1987 | Goldfarb et al. | |
| 4,683,587 | A | 7/1987 | Silverman | |
| 4,727,599 | A | 2/1988 | Rappaport et al. | |
| 4,819,647 | A | 4/1989 | Byers et al. | |
| 5,294,988 | A | 3/1994 | Wakabayashi et al. | |
| 5,386,084 | A | 1/1995 | Risko | |
| 5,603,726 | A | 2/1997 | Schulman et al. | |
| 5,637,417 | A * | 6/1997 | Engmark et al. | 429/97 |
| 5,824,022 | A | 10/1998 | Zilberman et al. | |
| 5,948,006 | A | 9/1999 | Mann | |
| 6,067,474 | A | 5/2000 | Schulman et al. | |
| 6,092,707 | A | 7/2000 | Bowes | |
| 6,272,382 | B1 * | 8/2001 | Faltys et al. | 607/57 |

(Continued)

FOREIGN PATENT DOCUMENTS

EP  1271898 A1  1/2003

(Continued)

OTHER PUBLICATIONS

Asyst Technologies Inc v. Empak Inc, 60 USPQ2d 1567, 1672-73 (Fed. Cir. 2001).*

(Continued)

*Primary Examiner* — Carl H Layno
*Assistant Examiner* — Natasha N Patel
(74) *Attorney, Agent, or Firm* — Henricks, Slavin & Holmes LLP

(57) ABSTRACT

A case for use with a speech processor unit including a housing configured to receive the speech processor unit and a connector configured to be connected to a connector on the speech processor unit.

5 Claims, 14 Drawing Sheets

U.S. PATENT DOCUMENTS

| | | | |
|---|---|---|---|
| 6,308,101 B1 * | 10/2001 | Faltys et al. | 607/57 |
| 6,390,971 B1 * | 5/2002 | Adams et al. | 600/25 |
| 6,396,769 B1 | 5/2002 | Polany | |
| 6,614,722 B2 | 9/2003 | Polany et al. | |
| 6,697,674 B2 | 2/2004 | Leysieffer | |
| 6,748,093 B2 | 6/2004 | Topholm | |
| 6,748,094 B1 * | 6/2004 | Tziviskos et al. | 381/330 |
| 6,761,266 B2 | 7/2004 | Popish | |
| 6,775,389 B2 * | 8/2004 | Harrison et al. | 381/330 |
| 6,778,858 B1 | 8/2004 | Peeters | |
| 6,810,289 B1 | 10/2004 | Shaquer | |
| 6,922,591 B2 | 7/2005 | Single | |
| 6,954,405 B2 | 10/2005 | Polany et al. | |
| 7,003,128 B2 | 2/2006 | Boonen | |
| 7,058,452 B2 * | 6/2006 | Dahlberg | 607/36 |
| 7,069,063 B2 | 6/2006 | Halkosaari et al. | |
| D528,213 S | 9/2006 | Darley et al. | |
| 7,113,611 B2 | 9/2006 | Leedom et al. | |
| 7,123,733 B1 | 10/2006 | Borowsky et al. | |
| 7,142,926 B2 | 11/2006 | Crawford | |
| 7,158,376 B2 | 1/2007 | Richardson et al. | |
| 7,167,572 B1 | 1/2007 | Harrison et al. | |
| 7,171,014 B2 | 1/2007 | Morales et al. | |
| 7,174,214 B2 | 2/2007 | Seligman | |
| 7,263,032 B2 | 8/2007 | Polany et al. | |
| 7,312,984 B2 | 12/2007 | Richardson et al. | |
| 7,400,917 B2 | 7/2008 | Wood et al. | |
| 7,535,799 B2 | 5/2009 | Polany et al. | |
| 7,630,772 B1 | 12/2009 | Walsh et al. | |
| 7,660,633 B2 | 2/2010 | Darley et al. | |
| 2002/0193136 A1 | 12/2002 | Halkosaari et al. | |
| 2003/0036782 A1 | 2/2003 | Hartley | |
| 2004/0073275 A1 * | 4/2004 | Maltan et al. | 607/57 |
| 2005/0181745 A1 | 8/2005 | Wood et al. | |
| 2007/0106344 A1 | 5/2007 | Darley et al. | |
| 2007/0270180 A1 | 11/2007 | Takagi | |
| 2008/0298627 A1 | 12/2008 | Bonebright et al. | |
| 2009/0017884 A1 | 1/2009 | Rotschild | |
| 2010/0137941 A1 | 6/2010 | Darley et al. | |
| 2010/0137942 A1 | 6/2010 | Darley et al. | |

FOREIGN PATENT DOCUMENTS

| | | |
|---|---|---|
| EP | 1271898 B1 | 4/2006 |
| WO | WO 01/87014 A2 | 11/2001 |
| WO | WO-2003/076012 A1 | 9/2003 |
| WO | WO 2005/007049 A1 | 1/2005 |
| WO | WO 2006/071210 A1 | 7/2006 |
| WO | WO 2007/102158 A2 | 9/2007 |
| WO | WO 2008/150642 A1 | 12/2008 |

OTHER PUBLICATIONS

In re Schreiber 128 F.3d 1473, 1477, 44 USPQ2d 1429, 1431 (Fed. Cir. 1997).*

Office Action dated Jan. 22, 2008 in related U.S. Appl. No. 11/121,700.

Office Action dated Jun. 9, 2008 in related U.S. Appl. No. 11/121,700.

Office Action dated Nov. 5, 2008 in related U.S. Appl. No. 11/121,700.

Advisory Action dated Dec. 29, 2008 in related U.S. Appl. No. 11/121,700.

Claims in related U.S. Appl. No. 11/121,700 as of Jan. 29, 2009.

Office Action dated Mar. 30, 2009 in related U.S. Appl. No. 11/121,700.

Claims in related U.S. Appl. No. 11/121,700 as of Jul. 28, 2009.

Notice of Allowance dated Oct. 26, 2009 in related U.S. Appl. No. 11/121,700.

Allowed Claims in related U.S. Appl. No. 11/121,700.

Claims in related U.S. Appl. No. 12/607,427 as of Jul. 25, 2011.

* cited by examiner

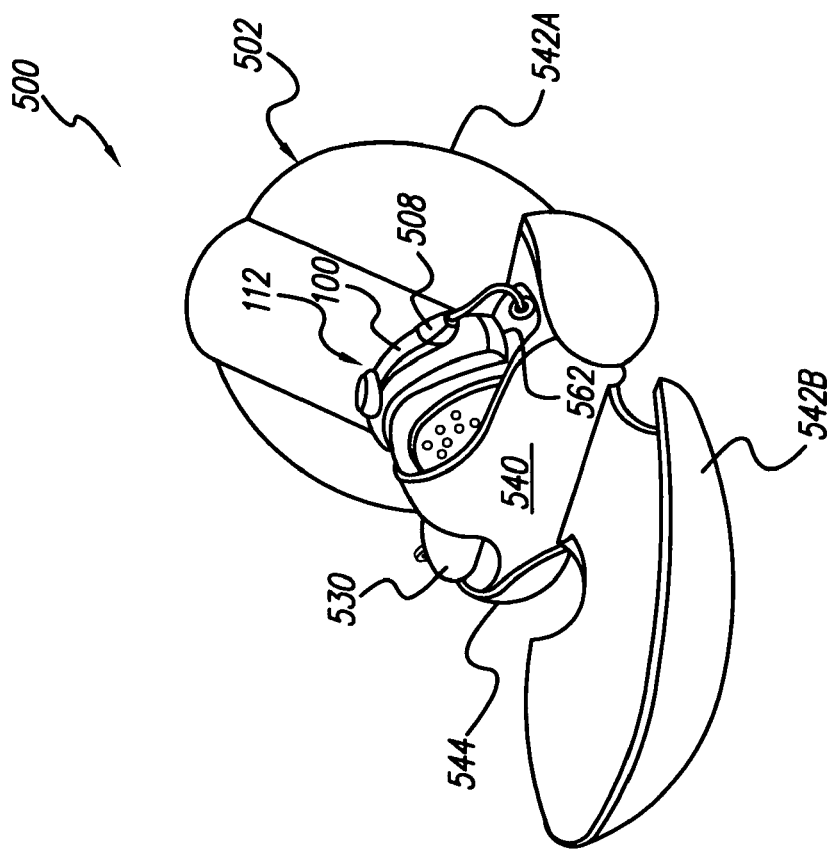
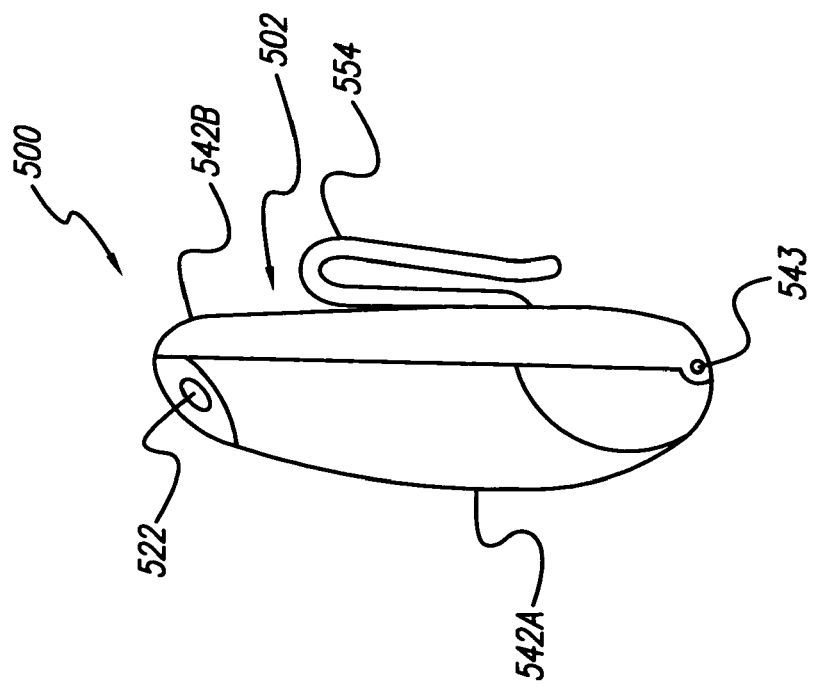
FIG. 12
FIG. 11

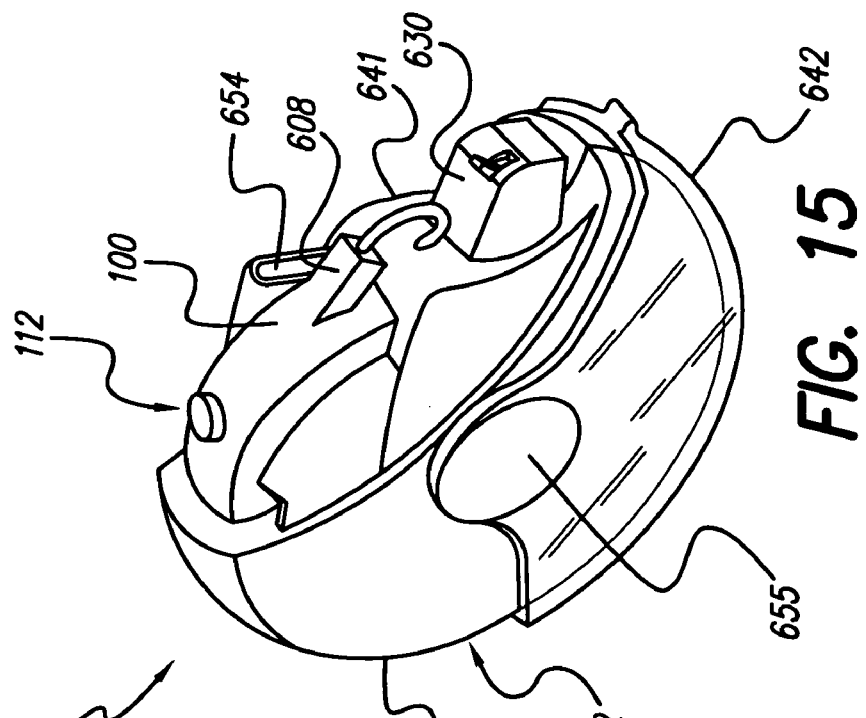
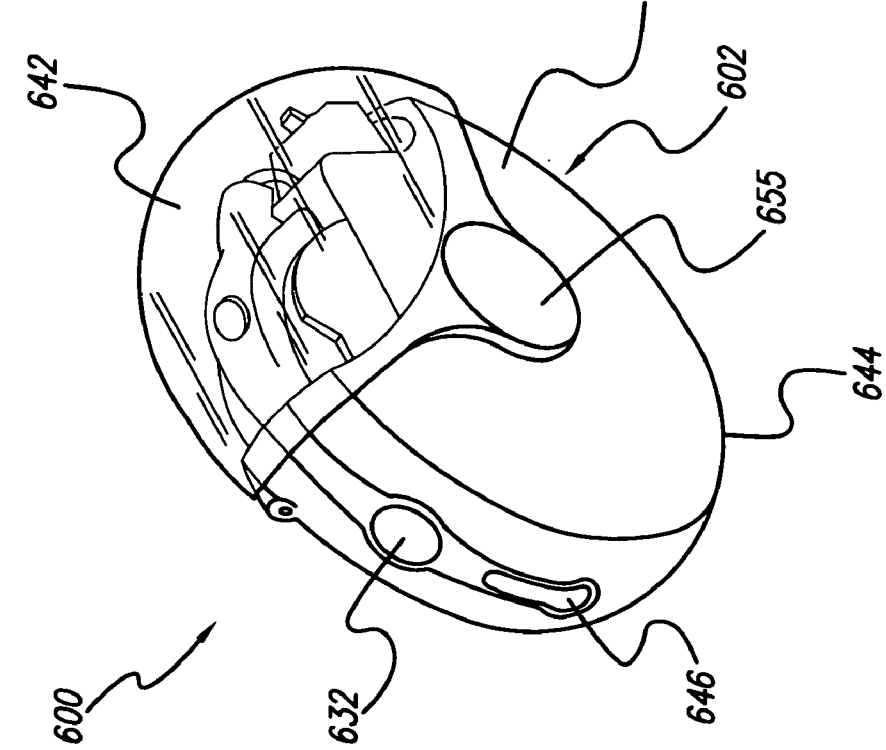

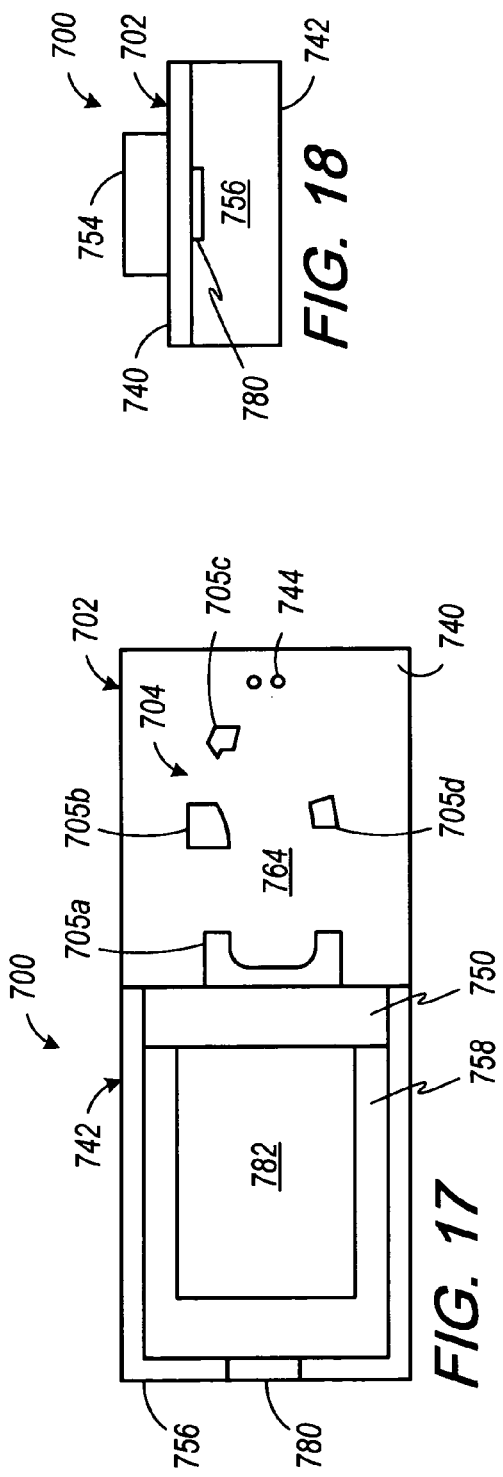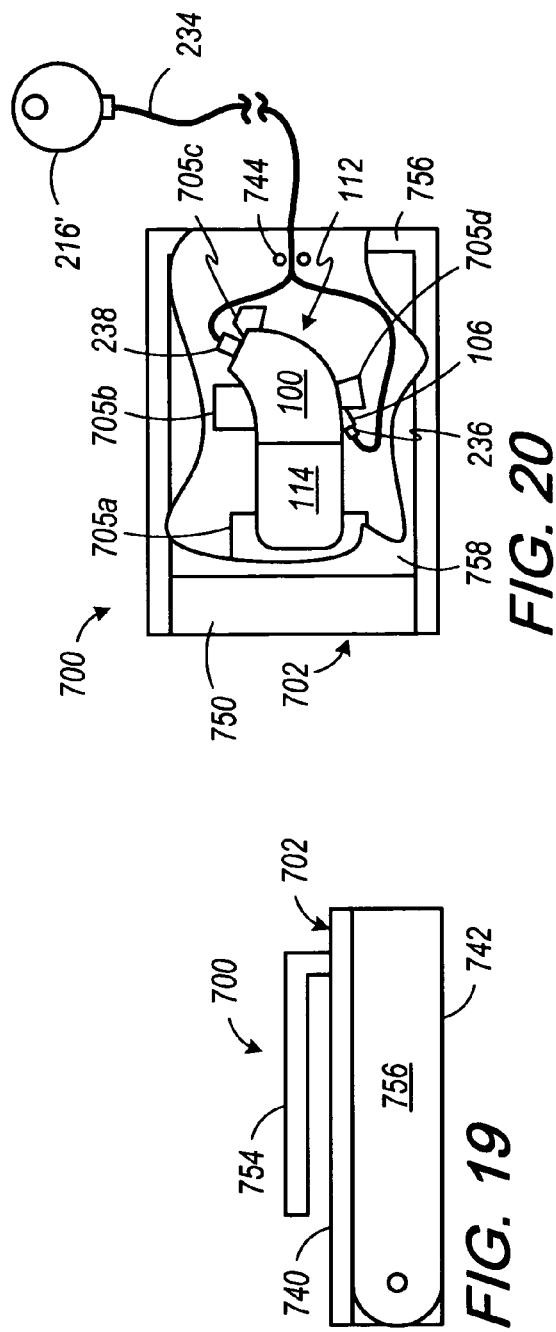

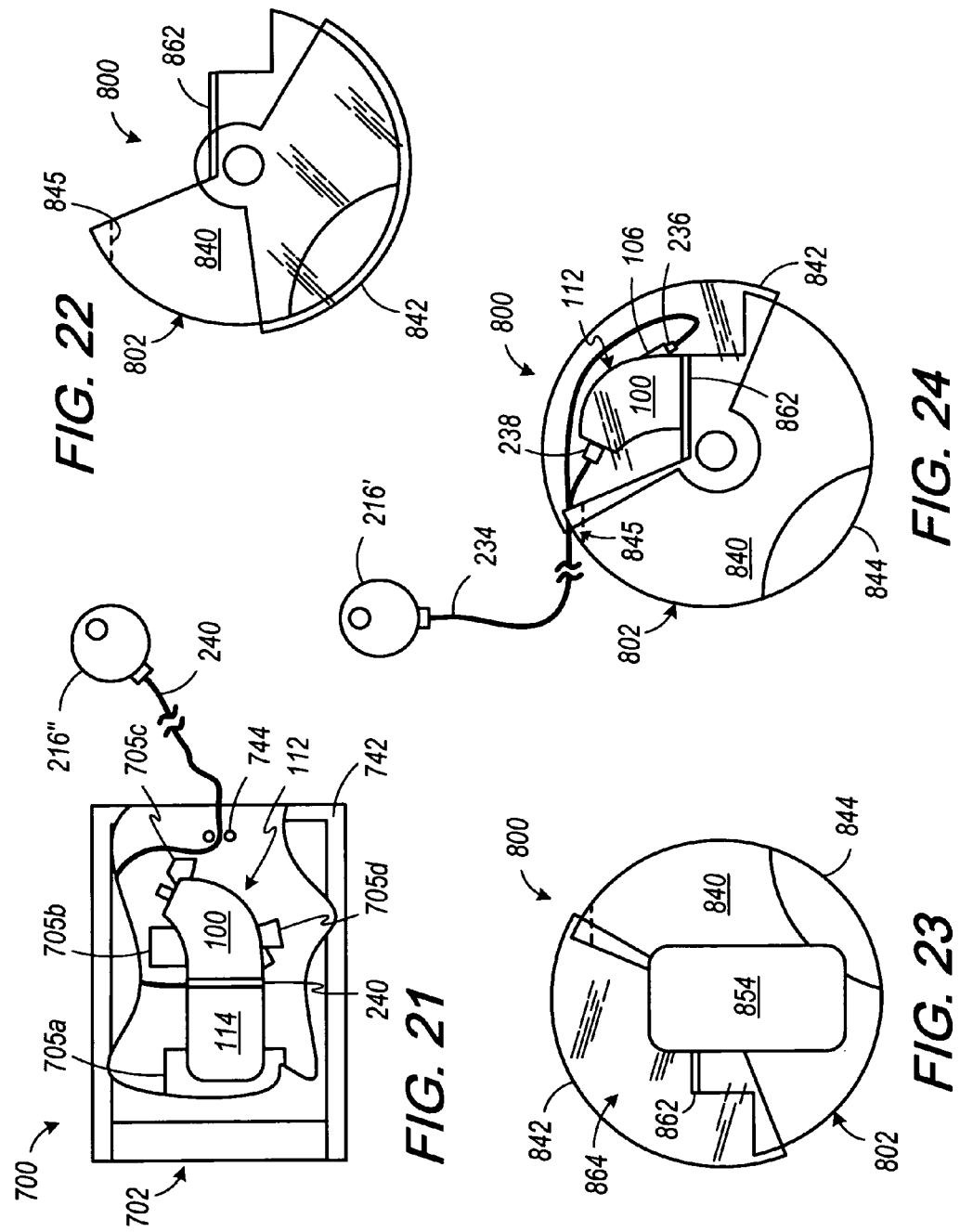

SPEECH PROCESSOR CASES

CROSS-REFERENCE TO RELATED APPLICATIONS

This application claims the benefit of and priority to previously filed U.S. Provisional Patent Application Ser. No. 60/568,450, filed May 5, 2004, which is entitled "Behind-The-Ear Speech Processor Case" and incorporated herein by reference in its entirety.

BACKGROUND OF THE INVENTIONS

1. Field of Inventions

The present inventions relate generally to speech processors such as, for example, the speech processors in implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a speech processor, converted to a pulse sequence having varying pulse widths and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. A representative ICS system is disclosed in U.S. Pat. No. 5,824,022, which is entitled "Cochlear Stimulation System Employing Behind-The-Ear Speech Processor With Remote Control" and incorporated herein by reference in its entirety.

As alluded to above, ICS systems typically include an implantable device, a speech processor unit, a microphone that is in communication with the speech processor unit, and a headpiece that is in communication with both the speech processor unit and the implantable device. In one type of ICS system, the speech processor unit is worn behind the ear and, accordingly, this type of speech processor unit is often referred to as a behind-the-ear speech processor unit (or "BTE unit"). The BTE unit is typically secured to the user with a removable ear hook and, in many cases, a microphone is carried by the ear hook. An on-board microphone is also carried by the BTE unit itself. Another type of speech processor unit is the body worn speech processor unit (or "body worn unit"). The body worn unit, which is larger and heavier than a BTE unit, is typically worn on the user's belt or carried in the user's pocket. Microphones used in combination with body worn units are often incorporated into the headpiece.

The present inventors have determined that conventional ICS systems are susceptible to improvement. For example, body worn units are preferable to BTE units in the case of infants and toddlers. BTE units tend to be too big for infants, and toddlers tend to remove and/or damage BTE units. Body worn units, on the other hand, can be attached to a harness that positions the speech processor unit on the infant or toddler's back, where it is difficult for the infant or toddler to reach. A BTE unit may, however, be more suitable once the child reaches an age (e.g. 5 years) at which he or she is less likely to damage the speech processor unit. Parents must then purchase a second speech processor unit, which is quite expensive. Even in those instances where insurance coverage or government subsidy (collectively "insurance") provides for two speech processor units, and the parents elect to receive a BTE unit in addition to the body worn unit, the body worn unit may be of limited utility once the child is old enough to switch to a BTE unit. Moreover, if the BTE unit is lost or damaged, the child will be forced to switch back to a body worn unit because there is no spare BTE unit.

The present inventors have also determined that adults face similar obstacles with respect to BTE units and body worn units. For example, many adults prefer the smaller BTE units for most everyday activities, but prefer body worn units for sports and other activities for which an ear hook mounted BTE unit is simply unsuitable. Here too, the user is faced with a choice—elect to obtain a BTE unit or a body worn unit through insurance and, if possible, purchase the other type of speech processor unit. Moreover, even in those instances where insurance provides for two speech processor units, the user will not have a spare BTE unit if he or she elects to obtain one of each. Users are also forced to carry both speech processor units with them if they intend to switch from the BTE unit to the body worn unit and back without returning home.

SUMMARY OF THE INVENTIONS

A speech processor case in accordance with a present invention includes a housing with a speech processor storage area, a first housing headpiece connector configured to be connected to the speech processor unit headpiece connector, and a second housing headpiece connector operably connected to the first housing headpiece connector and configured to be connected to a headpiece.

A speech processor case in accordance with one embodiment of a present invention includes a housing with a speech processor storage area and a housing power connector associated with the speech processor storage area and configured to be connected to the speech processor unit power connector.

A method in accordance with one implementation of a present invention includes the steps of positioning a behind-the-ear speech processor unit in a speech processor case, including at least one of a headpiece connector and a power connector, and connecting the behind-the-ear speech processor unit to the at least one of a headpiece connector and a power connector.

A method in accordance with one implementation of a present invention includes the steps of docking a behind-the-ear speech processor unit within a speech processor case and operably connecting the behind-the-ear speech processor unit to a cochlear implant by way of the speech processor case.

A case in accordance with one embodiment of a present invention includes a housing with a behind-the-ear sound unit storage area configured to receive behind-the-ear sound unit and means for mounting the behind-the-ear sound unit within the storage area.

Such cases and methods are advantageous for a variety of reasons. For example, the cases and methods allow the users of BTE units to enjoy the benefits of body worn units as well as a BTE unit without the expense associated with obtaining two speech processor units. More specifically, the present cases and methods allow a BTE unit to be converted into a body worn unit by simply placing the BTE unit into the case. While the BTE unit is safely stored within the case, apparatus that is conventionally connected directly to a BTE unit, such as a headpiece or a power supply, may instead be connected to the BTE unit by way of the connectors (or other instrumentalities) associated with the case. Other cases in accordance with the present inventions allow a headpiece to be directly coupled to a BTE unit. In either case, parents of infants and toddlers, as well as adults who enjoy switching from a BTE unit to a body worn unit and back, can obtain a BTE unit and a case instead of the considerably more expensive combination of a BTE unit and a body worn unit without any reduction in functionality.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of exemplary embodiments of the inventions will be made with reference to the accompanying drawings.

FIG. 3A is a flow chart illustrating a method in accordance with one embodiment of a present invention.

FIG. 11 is side view of a speech processor case in accordance with one embodiment of a present invention in a closed orientation.

FIG. 12 is perspective view of the speech processor case illustrated in FIG. 11 in an open orientation.

FIG. 14 is perspective view of a speech processor case in accordance with one embodiment of a present invention in a closed orientation.

FIG. 15 is perspective view of the speech processor case illustrated in FIG. 14 in an open orientation.

FIG. 17 is a plan view of a speech processor case in accordance with one embodiment of a present invention in an open orientation.

FIG. 18 is an end view of the speech processor case illustrated in FIG. 17 in a closed orientation.

FIG. 19 is a side view of the speech processor case illustrated in FIG. 17 in a closed orientation.

FIG. 20 is a cutaway view of the speech processor case illustrated in FIG. 17 in a closed orientation with a speech processor unit therein.

FIG. 21 is a cutaway view of a speech processor case in accordance with one embodiment of a present invention in a closed orientation with a speech processor unit therein.

FIG. 22 is a side view of a speech processor case in accordance with one embodiment of a present invention in an open orientation.

FIG. 23 is a side view of the speech processor case illustrated in FIG. 22 in a closed orientation.

FIG. 24 is a side view of the speech processor case illustrated in FIG. 22 in a closed orientation with a speech processor unit therein.

DETAILED DESCRIPTION OF THE EXEMPLARY EMBODIMENTS

This application is related to concurrently filed application Ser. No. 11/121,700, entitled "Methods of Converting A Behind-The-Ear Speech Processor Unit Into A Body Worn Speech Processor Unit."

The following is a detailed description of the best presently known modes of carrying out the inventions. This description is not to be taken in a limiting sense, but is made merely for the purpose of illustrating the general principles of the inventions. The detailed description is organized as follows:

I. Exemplary Speech Processors
II. Exemplary Speech Processor Cases

The section titles and overall organization of the present detailed description are for the purpose of convenience only and are not intended to limit the present inventions.

The present inventions have application in a wide variety of systems that provide sound (i.e. either sound or a perception of sound) to the hearing impaired as well as others who require such systems on a situational basis. One example of such a system is an ICS system where an external speech processor communicates with a cochlear implant and, accordingly, the present inventions are discussed in the context of ICS systems. The present inventions are not, however, limited to ICS systems and may be used in combination with other systems for the hearing impaired that currently exist, or are yet to be developed. For example, the present inventions are applicable to behind-the-ear "hearing aid" units that include digital signal processors.

I. Exemplary Speech Processor Units

Figure 1:
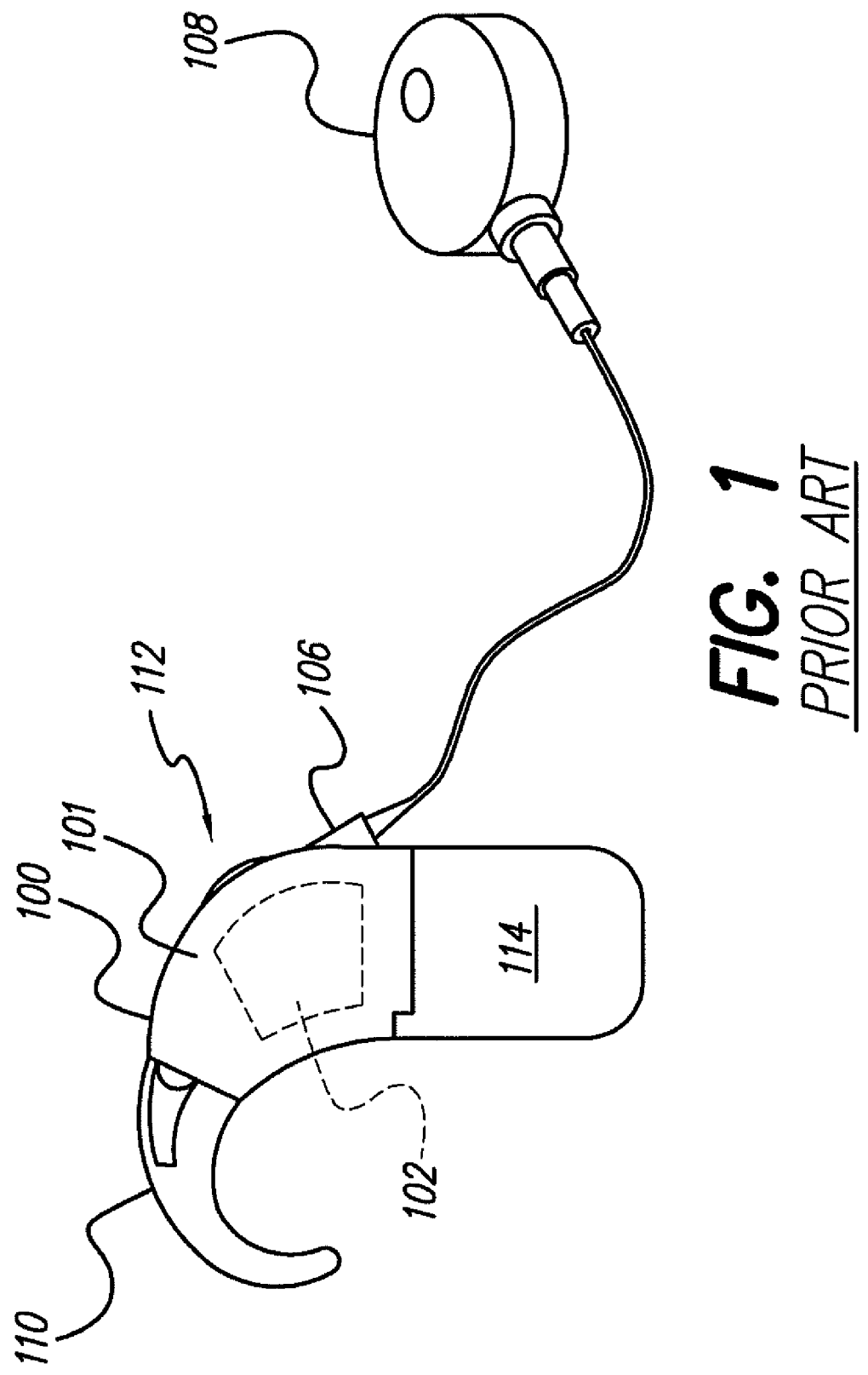
FIG. 1 is a perspective view of a conventional BTE unit and associated structures.
Figure 2:
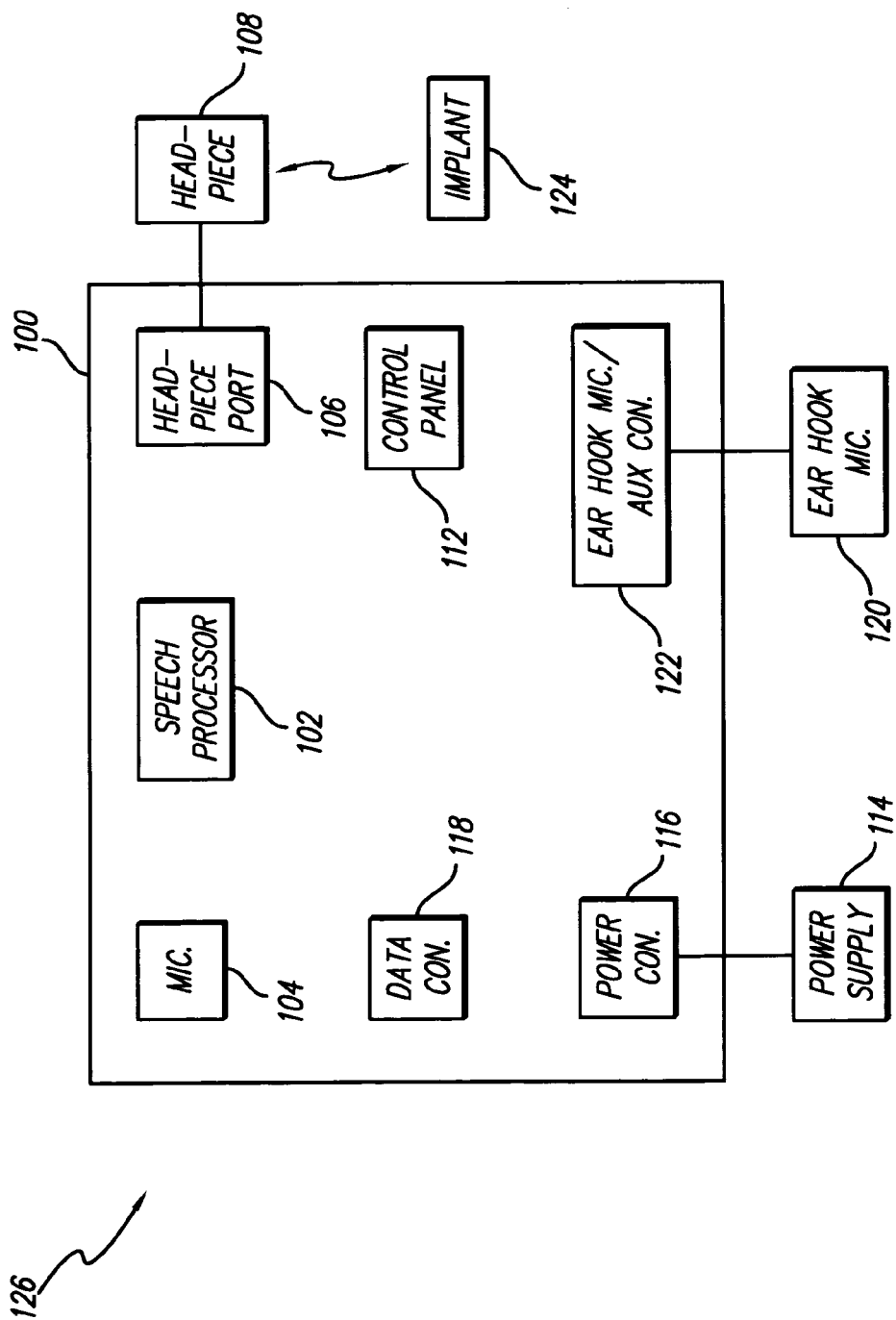
FIG. 2 is functional block diagram of an ICS system including the conventional BTE unit illustrated in FIG. 1.

One example of a speech processor unit which may be used in combination with, or form part of, the present inventions is the conventional BTE unit 100 illustrated in FIGS. 1 and 2. The BTE unit 100 includes an external housing 101, a speech processor 102 located within the external housing, an on-board microphone 104, a headpiece port 106 that allows the BTE unit to be connected to a headpiece 108, an ear hook 110, and a control panel 112. As used herein, the term "port" represents any and all suitable "male" or "female" electrical and/or electromechanical connector or other device which facilitates the communication between two devices. The exemplary control panel 112 includes a volume knob and a program switch. The BTE unit 100 is powered by a removable power supply 114 and, to that end, the BTE unit includes a power connector 116 in addition to a suitable mechanical connector for securing the power supply to the BTE unit. Suitable power supplies include rechargeable and disposable batteries or other electrochemical cells. One or more data connectors 118 are also provided. Such connectors may be used, for example, to connect the BTE unit 100 to a clinician's programming interface (CPI) unit, a clinician's fitting station, and/or other external devices in order to, for example, test and reprogram the operational parameters of the speech processor 102 and/or transfer a set of stimulation parameters directly to a speech processor unit. Finally, an additional microphone 120 may be mounted on the ear hook 110 and the exemplary BTE unit 100 includes a connector 122 for the ear hook microphone and/or an auxiliary device such as a mobile phone or a music player. The BTE unit 100 can be programmed to process sounds received by way of the on-board microphone 104, the ear hook microphone/auxiliary device connector 122, or some blend of the two.

During use, ambient sound pressure waves picked up by the on-board microphone 104, the ear hook microphone 120, and/or received from an auxiliary device are converted into electrical signals. The electrical signals are then processed by the speech processor 102, converted into a pulse sequence having varying pulse widths and/or amplitudes, and transmitted through the headpiece 108 to a receiver circuit in the implant 124. The implant 124 also includes an electrode array that is inserted into the cochlea of the inner ear. The electrical stimulation current generated by the implant is applied to varying electrode combinations to create a perception of sound. The BTE unit 100, headpiece 108 and implant 124 together define an ICS system 126.

Although the present inventions are not limited to any particular BTE units or ICS systems, one commercially available example of a suitable BTE unit is the HIRES™ AURIA™ BTE unit from Advanced Bionics Corporation in Sylmar, Calif. The present inventions are also not limited to BTE units that communicate with the implant by way of a headpiece. For example, BTE units that wirelessly communicate with the implant (i.e. without a headpiece and associated cable) may also be employed.

II. Exemplary Speech Processor Cases

Figure 3:
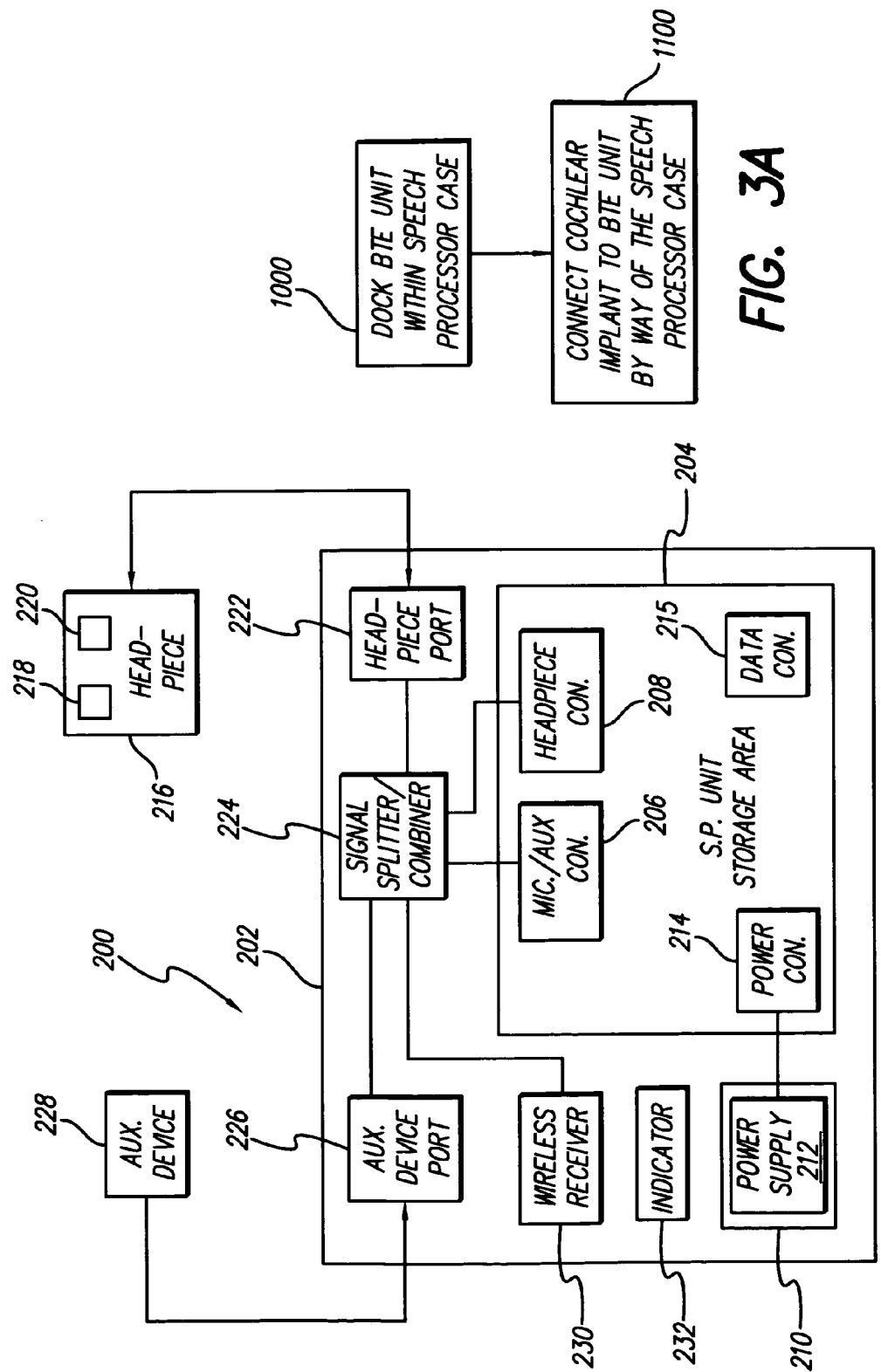
FIG. 3 is a functional block diagram of a speech processor case, a headpiece and an auxiliary device in accordance with one embodiment of a present invention.

FIG. 3 is a functional block diagram of a speech processor case (or "case") 200 with certain components that can be found in speech processor cases in accordance with many embodiments of the present inventions. Such a case may be used to store a conventional speech processor unit, such as a BTE unit, in such a manner that the case and BTE unit together form a body worn speech processor unit. Accordingly, the case allows a conventional BTE unit to function as a body worn unit as well as a BTE unit, which is also referred to herein as "converting" a BTE unit into a body worn unit. Additionally, although various cases are discussed in combination with the exemplary BTE unit 100 illustrated in FIGS. 1 and 2, the present inventions are not limited to any particular behind-the-ear units.

Referring more specifically to FIG. 3, the exemplary speech processor case 200 includes a housing 202 with a storage area 204 for a BTE unit, such as the BTE unit 100, or other speech processor unit. A plurality of connectors are associated with the storage area 204. The storage area and connectors associated therewith together define a BTE docking station. With respect to the connectors themselves, the case 200 is provided with a microphone/auxiliary device connector 206, which may be connected to the BTE unit ear hook microphone/auxiliary device connector 122, as well as a headpiece connector 208, which may be connected to the BTE headpiece port 106. The case 200 may also be provided with a power supply receptacle 210 for a power supply 212, such as disposable or rechargeable battery or other electrochemical cell, which may be used to power the BTE unit 100 when it is located within the case. To that end, the case 200 is provided with a power connector 214 that connects the power supply 212 to the BTE unit power connector 116, typically by way of electrical contacts associated with the power supply receptacle 210. In other words, the power connector 214 performs the function of non-permanently electrically connecting the power supply receptacle electrical contacts to the speech processor unit power connector when the speech processor unit is positioned within the speech processor storage area. The power supply 212 may also be used to power those aspects of the case 200 that require power. Additionally, in some instances, one or more data connectors 215 may be provided to couple the case 200 to the BTE unit data connector(s) 118.

The BTE microphone 104 will be located within the speech processor case 200 during use. As such, the exemplary case 200 may be used in combination with a headpiece 216 that, in addition to the circuitry 218 which communicates with the cochlear implant, also includes a microphone 220 that is used to pick up the ambient sound pressure waves. The headpiece 216 may be connected to the case microphone/auxiliary device connector 206 (and, therefore, the BTE unit ear hook microphone/auxiliary device connector 122) as well as to the headpiece connector 208 (and, therefore, to the BTE unit headpiece port 106) by way of a headpiece port 222 and a signal splitter/combiner 224. The signal splitter/combiner 224 demodulates the RF headpiece signal, which is modulated by the microphone signal, and also combines audio signals received by way of the headpiece port 222 and the auxiliary device port 226. In other words, the headpiece connector 208, the headpiece port 222 and the signal splitter/combiner 224 perform the function of establishing a communications link between the headpiece connector of a speech processor unit that is located within the speech processor storage area and a speech processor headpiece that is configured to transmit signals to an implanted cochlear stimulator and is located outside the housing. A suitable signal splitter/combiner is the signal splitter/combiner found in the Platinum Signal Processor body worn unit from Advanced Bionics Corporation. The signal splitter/combiner 224 also allows the signals to the implant communication circuitry 218 to reach only the headpiece connector 208, and signals from the headpiece microphone 220 to reach only the microphone connector/auxiliary device connector 206. The exemplary case 200 is also provided with an auxiliary device port 226 that allows an auxiliary device (e.g. a mobile phone, digital music player or the like) to be connected to the BTE unit 100 by way of the microphone connector/auxiliary device connector 206 and signal splitter/combiner 224.

The exemplary speech processor case 200 may also be provided with a wireless transceiver 230 such as, for example, an FM transceiver that allows wirelessly transmitted audio signals to be received by the BTE unit 100. Such transceivers allow students to receive wireless audio signals from a teacher who wears a wireless transmitter during class. The wireless transceiver 230 also allows the BTE unit 100 to transmit signals to a remote receiver. Such signals include status signals (e.g. a low battery signal to the teacher) and signals to an implantable device in those instances where there is no headpiece and the BTE unit transmits signals directly to the implantable device.

One or more audible, visible and/or otherwise perceptible indicator devices 232, such as a speaker or buzzer, an LED or other light source and/or a vibrator, may also be incorporated into the case 200. Such indicator devices 232 may be used to provide and audible, visible and/or otherwise perceptible indication as to the status of components of the BTE unit 100 and/or the case 200. Such indications may be provided when, for example, the power supply 212 is almost fully depleted, the BTE unit 100 is not properly docked within the case 200, or the headpiece 216 is dislodged.

Turning to FIG. 3A, some of the methods by which the speech processor cases disclosed herein may be used to allow a BTE unit to function as a body worn unit may briefly be summarized as follows. First, in Step 1000, the BTE unit is docked within the speech processor case. Next, in Step 1100, the cochlear implant is coupled to the BTE unit by way of the speech processor case. In some instances, Step 1100 may be accomplished in part by connecting a headpiece to the case.

Speech processor cases in accordance with the present inventions may be provided with additionally functionality. Such functionality is discussed below in the context of some of the illustrated embodiments.

Figure 4:
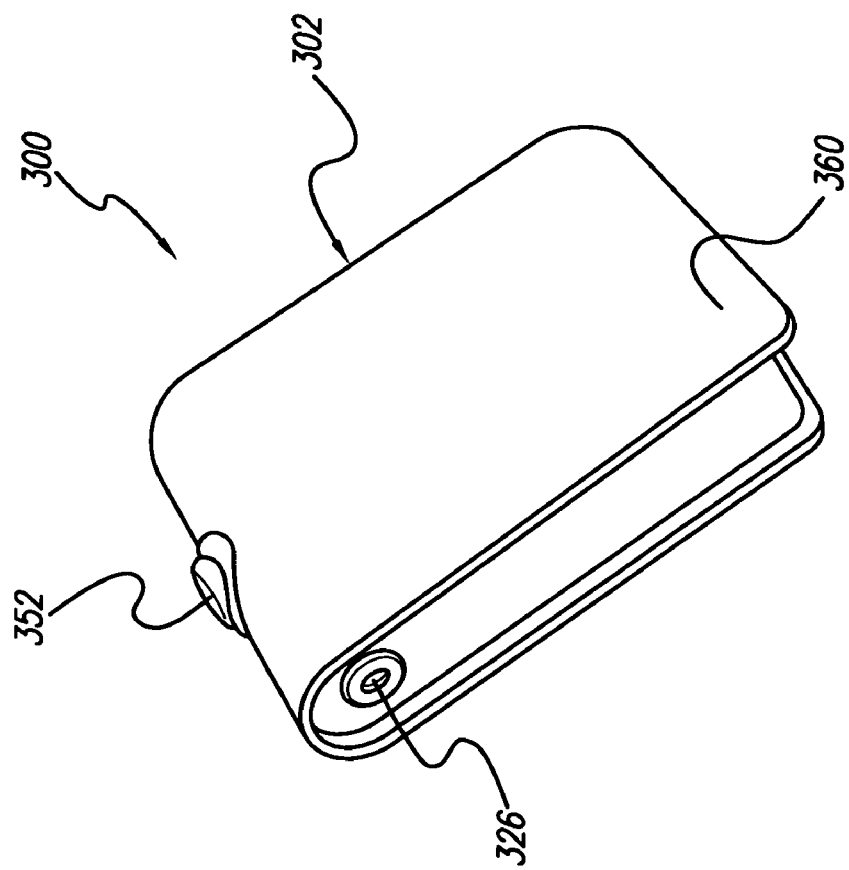
FIG. 4 is perspective view of a speech processor case in accordance with one embodiment of a present invention in a closed orientation.
Figure 5:
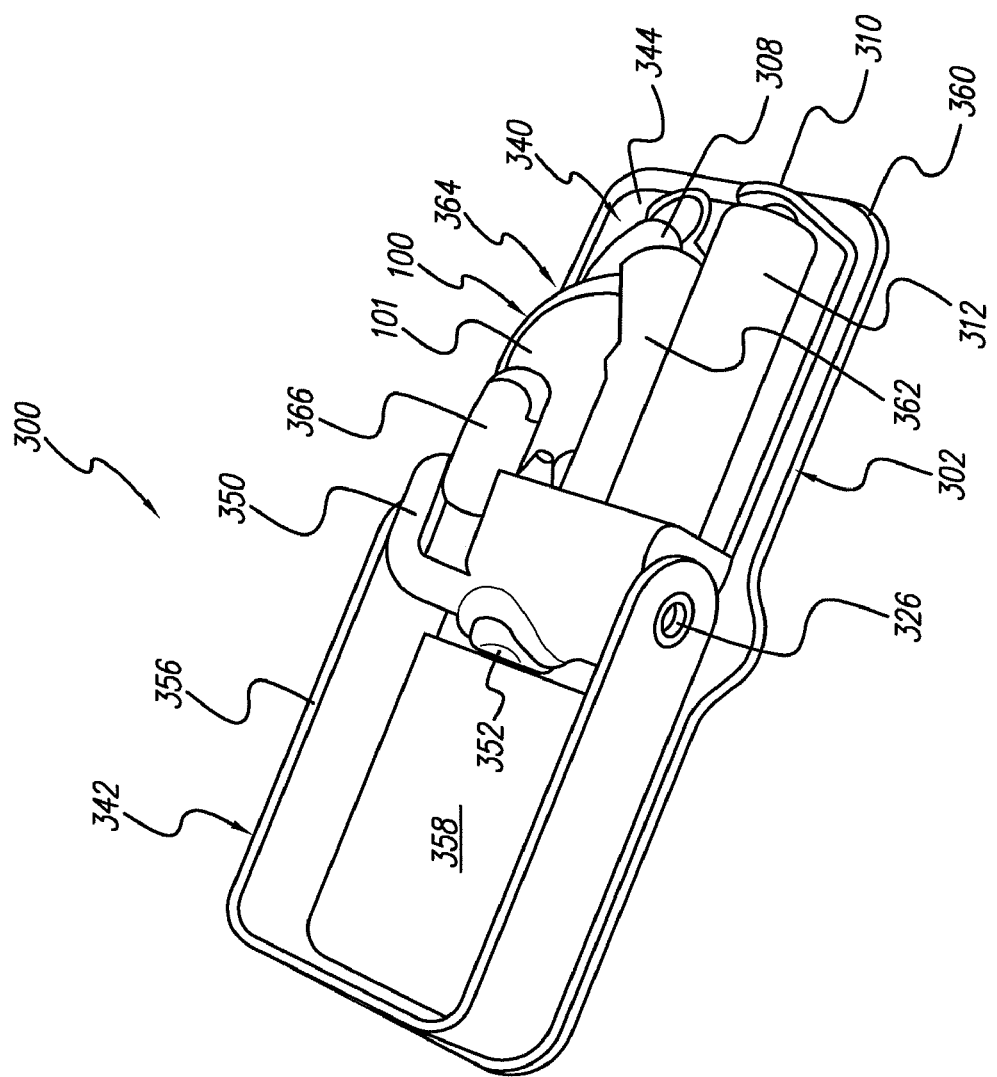
FIG. 5 is perspective view of the speech processor case illustrated in FIG. 4 in an open orientation.
Figure 6:
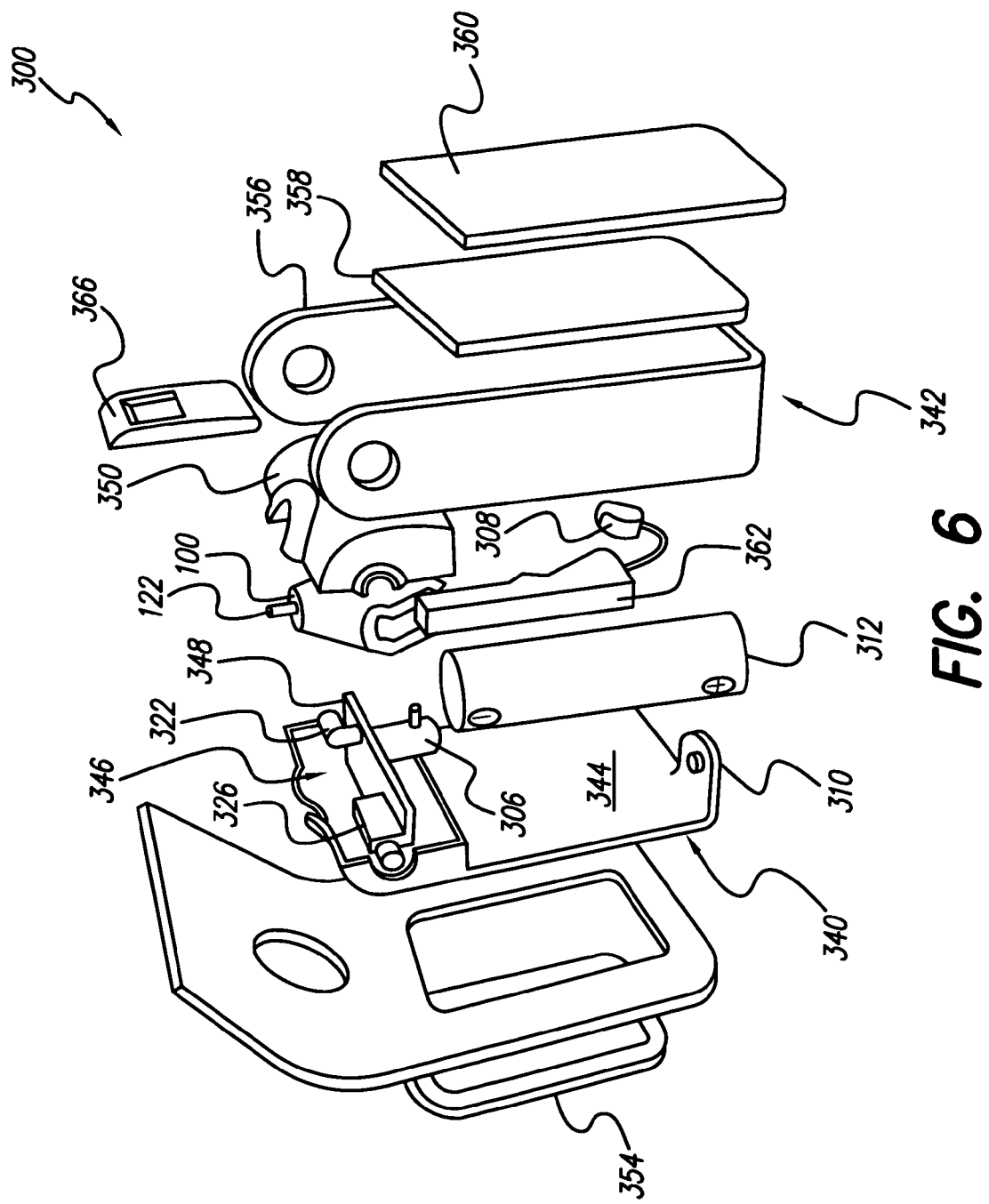
FIG. 6 is an exploded view of the speech processor case illustrated in FIG. 4.

The exemplary speech processor case 300 illustrated in FIGS. 4-6 may include some or all of the functional components discussed above in the context of FIG. 3 and similar functional components are represented by similar reference numerals. Referring first to the housing, the exemplary housing 302 includes a housing base member 340 and a housing cover 342 that is pivotable relative to the housing base member. The base member 340 includes a main portion 344, which defines a open region 346 for a circuit board 348, and a board cover 350. The circuit board 348 carries a case microphone/auxiliary device connector 306, a headpiece port 322, an auxiliary device port 326, and a signal splitter/combiner (not shown). The headpiece connector 308 (discussed below), the headpiece port 322 and the signal splitter/combiner perform the function of establishing a communications link between the headpiece connector of a speech processor unit that is located within the speech processor storage area and a speech processor headpiece that is configured to transmit signals to an implanted cochlear stimulator and is located outside the housing. The main portion 344 and board cover 350 together define four openings. Two of the openings facilitate access to the headpiece and auxiliary device ports 322 and 326, the microphone/auxiliary device connector 306 extends through one of the openings, and a volume control knob 352 extends through the final opening. The volume control knob 352 may be connected to an amplifier/attenuator on the circuit board 348 or, alternatively, may be connected to case data connector (s) 215 so that volume may be controlled at the BTE unit 100. A belt loop or clip 354, or other suitable mounting device (e.g. a lanyard ring or safety pin), is secured to the exterior of the main portion 344 and may be used to secure the case to the clothing or body of the user. With respect to power, the housing main portion 344 includes a power supply receptacle 310 for a battery or other power supply 312 (note FIGS. 5 and 6). The pivotable housing cover 342 consists of a U-shaped portion 356 and a flat portion 358 secured to the U-shaped portion. The U-shaped portion 356 also includes a pair of openings, which are aligned with two of the openings defined by the base member main portion 344 and board cover 350, to further facilitate access to the headpiece and auxiliary device ports 322 and 326.

The housing 302 is also provided with a user-changeable skin 360 which may be selectively secured to, or removed from, the housing for aesthetic purposes. A typical user would obtain a number of skins and cover the housing with the skin of his/her choice. The skin 360 may be attached to the housing base member main portion 344 and cover flat portion 358 though the use of snaps and other suitable instrumentalities. Exemplary materials for the skins include fabrics and plastics.

Turning to the manner in which the BTE unit 100 is docked within the exemplary case 300 illustrated in FIGS. 4-6, and connected to the various apparatus associated therewith, the case includes a guide rail 362 that can slidably receive the BTE unit when the case is in the open orientation illustrated in FIG. 5. As such, the area adjacent to the guide rail 362 defines the BTE storage area 364. The BTE unit 100 is inserted into the case 300 without the power supply 114. To that end, the guide rail 362 also includes a power connector (not shown) that is electrically connected to the power supply receptacle 310 and is positioned and configured such that it will mate with the BTE power connector 116. In other words, the guide rail power connector performs the function of non-permanently electrically connecting the power supply receptacle electrical contacts to the speech processor unit power connector when the speech processor unit is positioned within the speech processor storage area. Data connectors (not shown), which are associated with the guide rail 362, may be provided in order to connect to the BTE unit data connectors 118.

With respect to the connectors that are not carried by the guide rail 362 in the exemplary case 300, a slider 366 may be used to connect the microphone/auxiliary device connector 306 to the BTE unit ear hook microphone/auxiliary device connector 122. The slider 366 will be in a retracted state while the BTE unit is inserted into, or removed from, the case 300. A headpiece connector 308, which is connected to the case headpiece port 322, may be plugged into the BTE unit headpiece port 106 when the BTE unit 100 is in the case 300.

After the connections are made, the BTE unit 100 and case 300 will together define a body worn speech processor unit that may, for example, be mounted on an infant harness or the clothing of an adult. A headpiece (such as the headpiece 216 illustrated in FIG. 3) may be connected to the body worn unit so that the body worn unit can be used in conventional fashion.

Another exemplary speech processor case is generally represented by reference numeral 400 in FIGS. 7-10. Case 400 may include some or all of the functional components discussed above in the context of FIGS. 3-6 and similar functional components are represented by similar reference numerals. Referring first to the housing, the exemplary housing 402 includes a housing base member 440, a processor cover 442 that is rotatable relative to the base member, and a power supply cover 444. The base member 440 is formed by two essentially identical side portions 446a/446b (FIG. 10) which together define an internal region 447 for a circuit board 448, a power supply receptacle (not shown) and a battery 412 or other power supply. The internal region 447 is closed by an upper cover 450, a lower cover 452, and a front cover 453. The circuit board 448 carries a case microphone/auxiliary device connector 406, a headpiece port 422, an auxiliary device port 426, and a signal splitter/combiner (not shown). The headpiece connector 408 (discussed below), the headpiece port 422 and the signal splitter/combiner perform the function of establishing a communications link between the headpiece connector of a speech processor unit that is located within the speech processor storage area and a speech processor headpiece that is configured to transmit signals to an implanted cochlear stimulator and is located outside the housing, and the headpiece port 422 and the signal splitter/combiner perform the function of operably connecting the housing headpiece connector to a speech processor headpiece that is configured to transmit signals to an implanted cochlear stimulator. The headpiece and auxiliary device ports 422 and 426 are accessible through openings in the front cover 453. A belt loop or clip 454, or other suitable mounting device, is secured to the exterior of the side portion 446b and a name plate 455 is secured to the side portion 446a. The processor cover 442 consists of two essentially identical side pieces 456a/456b that are respectively rotatably secured to the base member side portions 446a/446b by the belt loop 454 and name plate 455.

Figure 8:
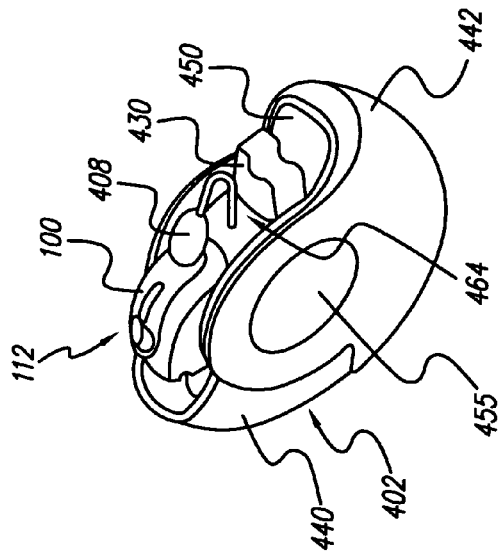
FIG. 8 is perspective view of the speech processor case illustrated in FIG. 7 in an open orientation.
Figure 9:
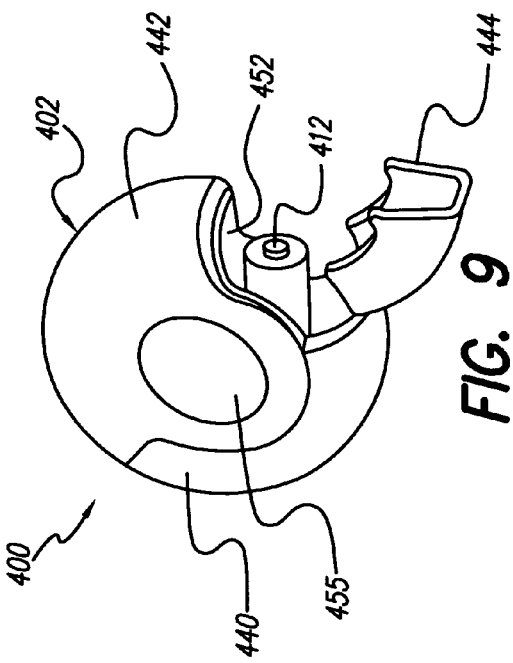
FIG. 9 is perspective view of the speech processor case illustrated in FIG. 7 with the power supply cover in an open orientation.

Turning to the manner in which the BTE unit 100 is docked within the exemplary case 400 illustrated in FIGS. 7-10, and connected to the various apparatus associated therewith, the case includes a guide rail 462 (FIG. 10) that can slidably receive the BTE unit when the processor cover 442 is in the open orientation (FIG. 8). The guide rail 462 is part of the upper cover 450 and the area between the upper cover and the inner surface of the processor cover 442 defines the BTE storage area 464. The BTE unit 100 is inserted into the case 400 without the power supply 114. To that end, the guide rail 462 also includes a power connector (not shown) that is electrically connected to the power supply 412 and is positioned and configured such that it will mate with the BTE power connector 116 and data connectors that will mate with the BTE unit data connectors 118. In other words, the guide rail power connector performs the function of non-permanently electrically connecting the power supply receptacle electrical contacts to the speech processor unit power connector when the speech processor unit is positioned within the speech processor storage area.

Figure 7:
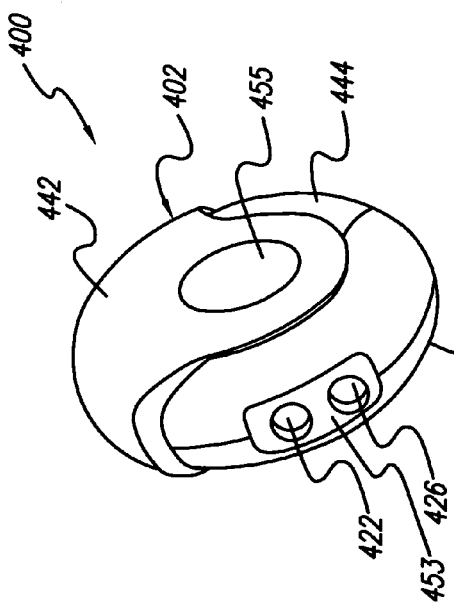
FIG. 7 is perspective view of a speech processor case in accordance with one embodiment of a present invention in a closed orientation.
Figure 10:
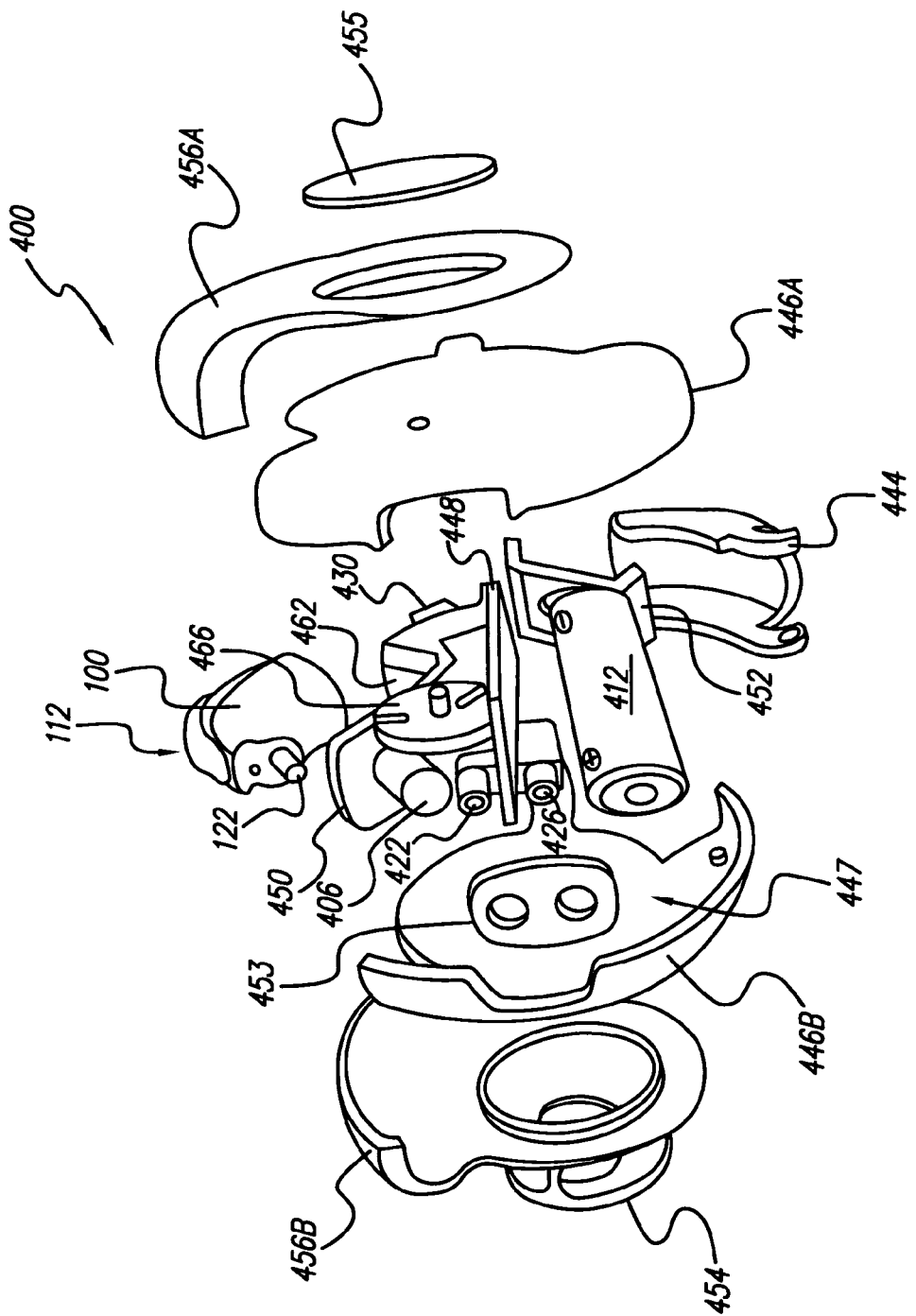
FIG. 10 is an exploded view of the speech processor case illustrated in FIG. 7.

As illustrated for example in FIG. 8, the BTE unit 100 is docked within the BTE storage area 464 such that the BTE control panel 112 is readily accessible when the processor cover 442 is moved to the open orientation. Put another way, and as illustrated in FIGS. 7 and 8, the guide rail 462 performs the function of docking the speech processor unit such that the user-manipulatable volume control device faces and is covered by the processor cover when the processor cover is in the closed orientation and is not covered by the processor cover when the processor cover is in the open orientation. Additionally, in the illustrated embodiment, the belt loop 454 is oriented relative to the housing base member 440 such that the BTE control panel 112 will face upwardly when worn on a belt.

With respect to the connectors that are not carried by the guide rail 462 in the exemplary case 400, a cam 466 (FIG. 10) may be used to connect the microphone/auxiliary device connector 406 to the BTE unit ear hook microphone/auxiliary device connector 122. The cam 466, which is connected to the case microphone/auxiliary device connector 406 and is engaged by the processor cover 442 over the 10-20% portion of the processor cover's range of motion that is closest to the fully closed orientation, drives the case microphone/auxiliary device connector a short distance toward the BTE unit ear hook microphone/auxiliary device connector 122 as the processor cover is closed. The cam 466 also drives the case microphone/auxiliary device connector 406 the same short distance in the opposite direction as the processor cover 442 is opened. A headpiece connector 408, which is connected to the case headpiece port 422, may be plugged into the BTE unit headpiece port 106 after the BTE unit 100 is positioned on the guide rail 462.

The exemplary case 400 is also provided with a wireless transceiver 430, such as an FM module, that is removably mounted within the BTE storage area 464 and connected to a corresponding port (not shown). The addition of the wireless transceiver 430 will, for example, allow a student to receive wireless audio signals from a teacher who wears a wireless transmitter during class. The wireless transceiver 430 also allows the BTE unit 100 to transmit signals to a remote receiver. Such signals include status signals (e.g. a low battery signal to the teacher) and signals to an implantable device in those instances where there is no headpiece and the BTE unit transmits signals directly to the implantable device.

The exemplary case 400 may also be configured such that it is child resistant in order to prevent children from obtaining access to the BTE unit 100 and/or the power supply 412. This will typically be accomplished by including child resistant latching mechanisms (not shown) on the housing base member 440 and processor cover 442 and/or housing base member and the power supply cover 444. Additionally, although the processor cover 442 may be substantially transparent so that the user can observe the BTE unit 100, processor covers on cases intended for use with children are preferably opaque (as shown in FIGS. 7-10) in order to prevent the child from seeing the BTE unit. In such instances, the case will typically include certain audible/visible indicator devices (discussed above with reference to FIG. 3 and below with reference to FIGS. 14-16) so that a parent or teacher will be able to stay apprised of the status of the BTE unit 100 and battery 412.

After the connections within the case 400 are made, the BTE unit 100 and the case will together define a body worn speech processor unit that may, for example, be mounted on an infant harness or the clothing of an adult. A headpiece (such as the headpiece 216 illustrated in FIG. 3) may be connected to the body worn unit so that the body worn unit can be used in conventional fashion.

Figure 13:
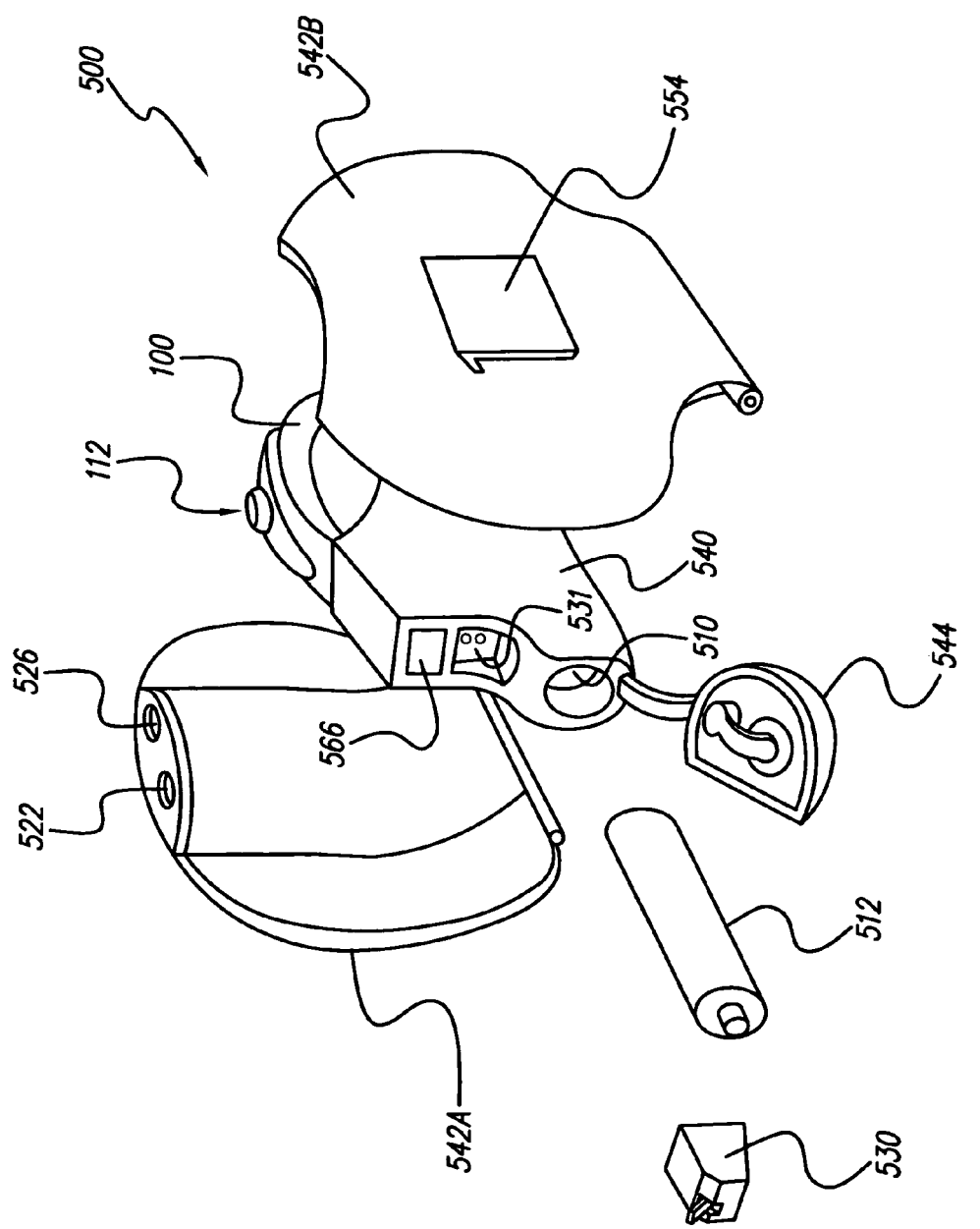
FIG. 13 is an exploded view of the speech processor case illustrated in FIG. 11.

Another exemplary speech processor case, which is generally represented by reference numeral 500 in FIGS. 11-13, may include some or all of the functional components discussed above in the context of FIGS. 3-10 and similar functional components are represented by similar reference numerals. Referring first to the housing, the exemplary housing 502 includes a BTE support portion 540 and a pair of covers 542a and 542b that are pivotably connected to the BTE support portion by a hinge 543. The BTE support portion 540 encloses a circuit board with a signal splitter/combiner (not shown), a case microphone/auxiliary device connector (also not shown), and a power supply receptacle 510 for a battery 512 or other suitable power supply. The power supply receptacle 510 is closed by a cover 544. The BTE support portion 540 also includes a port 531 for a wireless transceiver 530. The housing cover 542a carries a headpiece port 522 and an auxiliary device port 326, which are connected to the circuit board by way of, for example, a ribbon cable that extends though part of the hinge 543. The headpiece connector 508 (discussed below), the headpiece port 522 and the signal splitter/combiner perform the function of establishing a communications link between the headpiece connector of a speech processor unit that is located within the speech processor storage area and a speech processor headpiece that is configured to transmit signals to an implanted cochlear stimulator and is located outside the housing, and the headpiece port 522 and the signal splitter/combiner perform the function of operably connecting the housing headpiece connector to a speech processor headpiece that is configured to transmit signals to an implanted cochlear stimulator. A belt loop or clip 554, or other suitable mounting device, is secured to the exterior of the housing cover 542b.

The BTE unit 100 is docked within the exemplary case 500, and connected to various apparatus associated therewith, through the use of a guide rail 562 that slidably receives the BTE unit. The area between the guide rail 562 and the inner surfaces of the covers 542a and 542b defines the BTE storage area 564. As illustrated in FIGS. 11 and 12, the guide rail 562 performs the function of docking the speech processor unit such that the user-manipulatable volume control device faces and is covered by the processor covers when the processor covers are in the closed orientation and is not covered by the processor covers when the processor covers are in the open orientation. The BTE unit 100 is inserted into the case 500 without the power supply 114 and the guide rail 562 includes a power connector (not shown) that is electrically connected to the power supply receptacle 510. In other words, the guide rail power connector performs the function of non-permanently electrically connecting the power supply receptacle electrical contacts to the speech processor unit power connector when the speech processor unit is positioned within the speech processor storage area. The power connector is positioned and configured such that it will mate with the BTE power connector 116. Data connectors (not shown), which are associated with the guide rail 562, may be provided in order to connect to the BTE unit data connectors 118.

With respect to the connectors that are not carried by the guide rail 562 in the exemplary case 500, a button 566 may be used to connect the microphone/auxiliary device connector (not shown) to the BTE unit ear hook microphone/auxiliary device connector 122. The button 566 is preferably a spring biased button that alternately connects and disconnects the case microphone/auxiliary device connector and the BTE unit ear hook microphone/auxiliary device connector 122 when pressed. A headpiece connector 508, which is connected to the case headpiece port 522, may be plugged into the BTE unit headpiece port 106 when the BTE unit 100 is in the case 500.

After the connections are made, the BTE unit 100 and case 500 will together define a body worn speech processor unit that may, for example, be mounted on an infant harness or the clothing of an adult. A headpiece (such as the headpiece 216 illustrated in FIG. 3) may be connected to the body worn unit so that the body worn unit can be used in conventional fashion.

Figure 16:
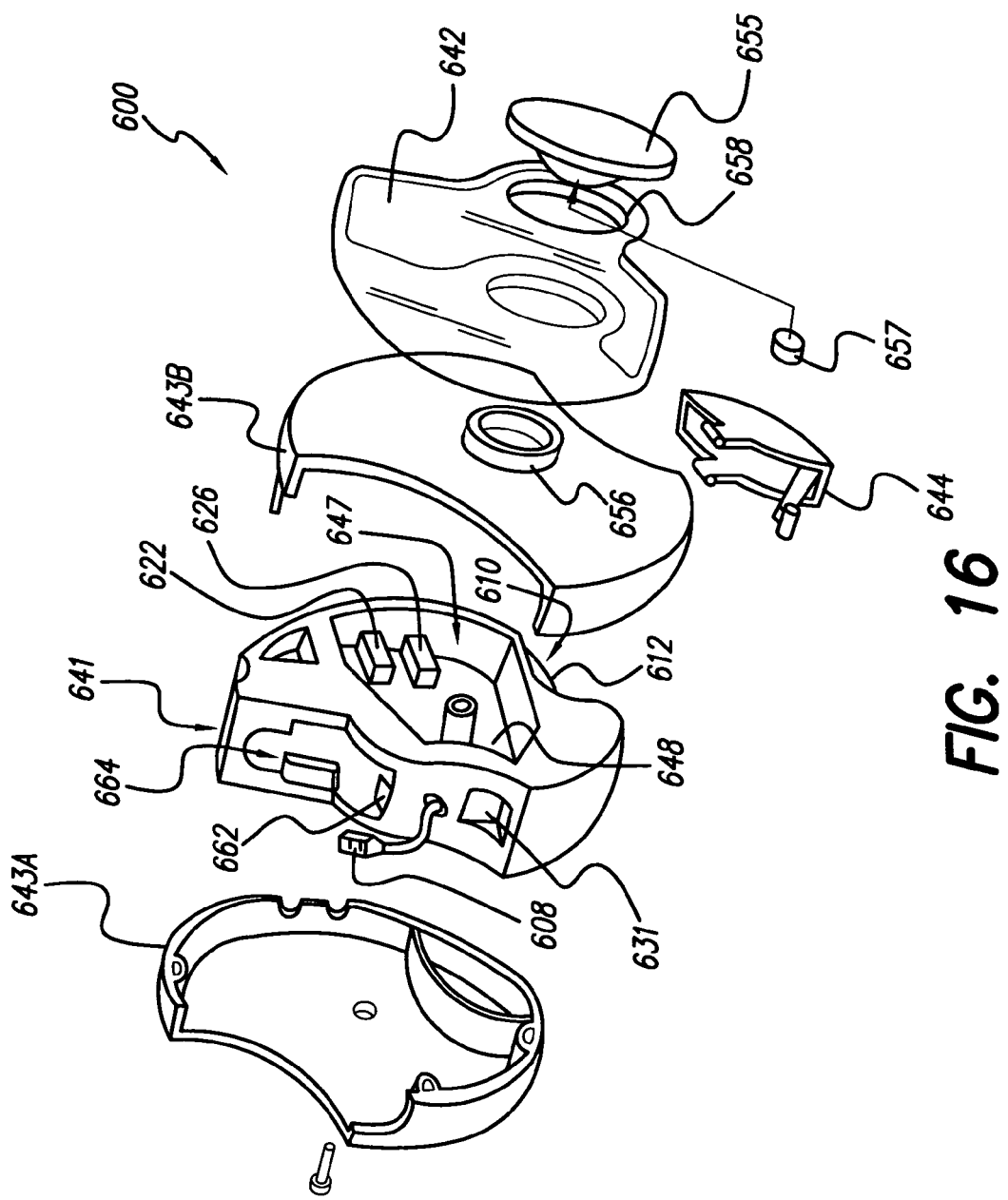
FIG. 16 is an exploded view of the speech processor case illustrated in FIG. 14.

Still another exemplary speech processor case, which is generally represented by reference numeral 600, is illustrated in FIGS. 14-16. Case 600 may include some or all of the functional components discussed above in the context of FIGS. 3-13 and similar functional components are represented by similar reference numerals. Referring first to the housing, the exemplary housing 602 includes a base member 640, a processor cover 642 that is rotatable relative to the base member, and a power supply cover 644. The housing base member 640 consists primarily of a center portion 641 and a pair of side portions 643a/643b. The center portion 641 defines an internal region 647 for a circuit board 648 as well as a power supply receptacle 610 for a battery 612 or other power supply. The base member internal region 647 is covered by the side portions 643a/643b. The circuit board 648 carries a headpiece port 622, an auxiliary device port 626, and a signal splitter/combiner (not shown). The headpiece connector 608 (discussed below), the headpiece port 622 and the signal splitter/combiner perform the function of establishing a communications link between the headpiece connector of a speech processor unit that is located within the speech processor storage area and a speech processor headpiece that is configured to transmit signals to an implanted cochlear stimulator and is located outside the housing, and the headpiece port 622 and the signal splitter/combiner perform the function of operably connecting the housing headpiece connector to a speech processor headpiece that is configured to transmit signals to an implanted cochlear stimulator. The headpiece and auxiliary device ports 622 and 626 are accessible through an opening in the center portion 641, which is covered by a resilient port cover 646. A belt loop or clip 654, or other suitable mounting device, is secured to the exterior of the side portion 643a and a name plate 655 is secured to the side portion 643b by a magnet 657. The processor cover 642 is rotatably mounted on housing base member 640. More specifically, the side portions 643a/643b each include a mounting ring 656 (only one visible) and the processor cover 642 includes a pair of corresponding apertures 658. The belt clip 654 and nameplate 655 hold the processor cover 642 in place.

With respect to the manner by which the BTE unit 100 is docked within the exemplary case 600 and connected to the various apparatus associated therewith, the case includes a guide rail 662 (FIG. 16) that can slidably receive the BTE unit when the case is in the open orientation (FIG. 15). The guide rail 662 is part of the base member center portion 641 and the area between the guide rail and the inner surface of the processor cover 642 defines the BTE storage area 664. As illustrated in FIGS. 14 and 15, the guide rail 662 performs the function of docking the speech processor unit such that the user-manipulatable volume control device faces and is covered by the processor cover when the processor cover is in the closed orientation and is not covered by the processor cover when the processor cover is in the open orientation. The BTE unit 100 is inserted into the case 600 without the power supply 114 and the guide rail 662 also includes a power connector (not shown) that is electrically connected to the battery 612 and is positioned and configured such that it will mate with the BTE power connector 116 and data connectors (not shown) that will mate with the BTE unit data connectors 118. In other words, the guide rail power connector performs the function of non-permanently electrically connecting the power supply receptacle electrical contacts to the speech processor unit power connector when the speech processor unit is positioned within the speech processor storage area. The case microphone/auxiliary device connector (not shown) is also supported on the base member center portion 641 in such a manner that it will mate with the BTE unit ear hook microphone/auxiliary device connector 122. A mechanism such as, for example, a cam similar to that described above with respect to FIGS. 7-10, may be provided in order to insure proper connection of the case and ear hook microphone/auxiliary device connectors. A headpiece connector 608, which is connected to the case headpiece port 622, may be plugged into the BTE unit headpiece port 106 after the BTE unit 100 is positioned on the guide rail 662. The exemplary case 600 is also provided with a wireless transceiver 630, such as an FM module, that is removably mounted within the BTE storage area 664 and connected to a corresponding port 631.

The exemplary case 600 is configured such that the BTE unit 100 is readily visible to the user. Referring more specifically to FIGS. 14 and 15, the belt loop 654 is oriented relative to the housing 602 such that the BTE control panel 112 will face upwardly when the case 600 is worn on a belt. The processor cover 642 is also substantially transparent so that the user can observe the BTE unit 100, its control panel 112 and any visible indicators, when the processor cover is in the closed orientation. The orientation of the BTE unit 100 within the storage area 664 also makes it easy to manipulate devices on BTE control panel 112 (e.g., the volume knob) when the processor cover 642 is in the open orientation.

Finally, the exemplary speech processor case 600 includes a visible indicator 632, such as an LED, which may be used to provide the status of components of the BTE unit 100 and/or the case 600. Such indications may be provided when, for example, the power supply 612 is almost fully depleted, the BTE unit 100 is not properly docked within the case 600, or the headpiece 216 is dislodged.

After the connections within the case 600 are made, the BTE unit 100 and the case will together define a body worn speech processor unit that may, for example, be mounted on an infant harness or the clothing of an adult. A headpiece (such as the headpiece 216 illustrated in FIG. 3) may be connected to the body worn unit so that the body worn unit can be used in conventional fashion.

Another exemplary speech processor case is generally represented by reference numeral 700 in FIGS. 17-20. Unlike the cases illustrated in FIGS. 3-16, the exemplary case 700 does not include the various ports, connectors and circuitry described above. Nor does the case 700 include its own power supply. Instead, the exemplary case 700 allows a headpiece to be directly coupled to the BTE unit 100. Power for the BTE unit 100 is supplied by the removable power supply 114.

Referring first to FIGS. 17-19, the case 700 consists of a housing 702 and a mounting device 704 that performs the function of securely holding the BTE unit 100 within the housing. The housing 702 includes a housing base member 740 and a housing cover 742 that is pivotable relative to the base member. In addition to carrying the mounting device 704 and a belt clip 754, the base member 740 includes a cable guide 744 that is discussed below with reference to FIG. 20. The housing cover 742 consists of a U-shaped portion 756 that is pivotably secured to the base member 740 by a hinge 750, and a flat portion 758 that is secured to the U-shaped portion. The U-shaped portion 756 includes an opening 780 that is adjacent to, and in line with, the cable guide 744 when the housing cover 742 is in the closed orientation. The opening 780 may, in some instances, include a resilient seal (not shown) that conforms to the headpiece cable when the housing 702 is closed and prevents moisture, dirt and/or dust from entering the housing through the opening. A user-changeable skin (not shown), such as that discussible with reference to FIGS. 4-6, may also be carried by the housing 702.

The mounting device 704 may be any suitable structure that holds the BTE unit 100 in place and, preferably, does so without blocking the control panel 112 so that the user can continue to access the control panel after the BTE unit is secured by the mounting device. The mounting device 704 in the illustrated embodiment includes a plurality of resilient members 705a-d (FIGS. 17 and 20) which have inner surfaces that together define a storage area 764 that corresponds to the shape of the exterior surface of the BTE unit 100 and power supply 114. The storage area 764 is preferably slightly smaller than the BTE unit 100 and power supply 114 so as to create an interference fit when the BTE unit and power supply are mounted therein. Other suitable mounting devices include, for example, one or more resilient straps or a guide rail. The housing cover 742 may also include a resilient pad 782 that is positioned and configured such that it will be aligned with the storage area 764 and engage the BTE unit 100 when the housing 702 is closed. The mounting device 704 may, as another alternative to the resilient members 705a-d, be in the form of a resilient pad that is positioned in such a manner that the BTE unit will be "sandwiched" between the resilient pads when the housing 702 is closed.

The BTE unit 100 may be connected to a headpiece 216' and mounted within the exemplary case 700 in the manner illustrated in FIG. 20. The headpiece 216' is similar to the headpiece 216 illustrated in FIG. 3 in that the headpiece 216' has circuitry that communicates with a cochlear implant and a microphone that picks up ambient sound pressure waves. Here, however, the headpiece signal is not modulated by the microphone signal and, instead, the headpiece and microphone signals are carried by separate wires within a headpiece cable 234. The end of the cable 234 opposite the headpiece 216' splits into two parts. The portion with the wire(s) that carry the headpiece signal is coupled to the BTE unit headpiece port 106 by a connector 236, while the portion with the wire(s) that carry the microphone signal is coupled to the BTE unit ear hook microphone/auxiliary device connector 122 (visible in FIG. 6) by a connector 238.

It should also be noted that, in those instances where the case 700 is intended to be used with a speech processor that is capable of wirelessly communicating with the headpiece, the cable guide 744 and opening 780 may be omitted.

The BTE unit 100 and case 700 together define a body worn speech processor unit that may, for example, be mounted on an infant harness or the clothing of an adult. The body worn unit may be assembled by securing the BTE unit within the housing 702 with the mounting device 704. The headpiece cable 234, which may be connected to the BTE unit 100 before or after the BTE unit is secured to the mounting device 704, may then be positioned in the cable guide 744 so that the cable 234 will extend though the opening 780 to the headpiece 216' when the cover 742 is closed.

As illustrated for example in FIG. 21, the exemplary speech processor case 700 may also be used in conjunction with a headpiece 216" that is connected to the BTE unit 100 by way of the BTE unit data connectors 118 (note FIG. 2). The headpiece 216", which includes a microphone as well as circuitry that communicates with a cochlear implant, is connected to the BTE unit 100 by way of a cable 240 and a connector 242. The headpiece and microphone signals are carried by separate wires within the headpiece cable 240, and the connector 242 couples the wires to the appropriate BTE data connectors 118. With respect to power, the connector 242 is also configured to couple the power supply 114 to the BTE unit power connector 116 (note FIG. 2).

Another exemplary speech processor case is illustrated in FIGS. 22-24. The speech processor case 800 is similar to the case illustrated in FIGS. 17-20 in that it does not include the ports, connectors and circuitry described above with reference to FIGS. 3-16. Case 800 is, however, configured to store an on-board power supply that powers the BTE unit 100 in essentially the same manner as the case 600.

The exemplary housing 802 is similar to the housing 602 (FIGS. 14-16) in that the housing 802 includes a base member 840, a processor cover 842 that is rotatable relative to the base member, and a power supply cover 844. The base member 840 includes a power supply receptacle (not shown) for a battery or other power supply (not shown). A belt loop or clip 854, or other suitable mounting device, is secured to the exterior of the housing 802. The case 800 is also provided with a guide rail 862 that can slidably receive the BTE unit 100 and securely mount the BTE unit within the case. The area between the guide rail 862 and the inner surface of the processor cover 842 defines the BTE storage area 864 (FIG. 23). The guide rail 862 also includes a power connector (not shown) that is electrically connected to the case power supply and is positioned and configured such that it will mate with the BTE power connector 116 (FIG. 2) when the BTE unit 100 is mounted within the case 800.

The exemplary case 800 is configured such that the BTE unit 100 is readily visible to the user. More specifically, the belt loop 854 is oriented relative to the housing 802 such that the BTE control panel 112 will face upwardly when the case 800 is worn on a belt. The processor cover 842 is also substantially transparent so that the user can observe the BTE unit 100, its control panel 112 and any visible indicators, when the processor cover is in the closed orientation. The orientation of the BTE unit 100 also makes it easy to manipulate devices on BTE control panel 112 (e.g., the volume knob) when the processor cover 842 is in the open orientation.

The BTE unit 100 may be connected to a headpiece 216' in the manner described above with reference to FIG. 20. More specifically, the wire(s) in the cable 234 that carry the microphone signal are coupled to the BTE unit ear hook microphone/auxiliary device connector by a connector 238, and the wire(s) that carry the headpiece signal are coupled to the BTE unit headpiece port 106 by a connector 236. The base member 840 may include a cable slot 845 that allows the processor cover 842 to close without damaging the cable 234 (note FIG. 24). A similar slot may alternatively, or in addition, be formed in the processor cover 842. However, in those instances where the case 800 is intended to be used with a speech processor that is capable of wirelessly communicating with the headpiece, the slot(s) may be omitted.

After the BTE unit 100 is mounted within the case 800, the BTE unit and case will together define a body worn speech processor unit that may, for example, be mounted on an infant harness or the clothing of an adult.

With respect to materials and dimensions, cases in accordance with the present inventions may be formed from any suitable metal or plastic materials. The dimensions will typically depend on the dimensions of the speech processor unit intended to be docked therein. For example, a case intended for use with BTE units would typically be about 50-100 mm long, about 50-100 mm wide and about 20-30 mm thick. However, the size may be increased as needed in order to, for example, provide additional case functionality.

The speech processor cases described above with reference to FIGS. 3-24 may include a wide variety of additional devices that provide additional functionality and/or augment existing functionality. For example, the speech processor case power supply may be used to charge the BTE unit 100 removable power supply 114 while the BTE unit is used in combination with the case. This may be accomplished by providing a physical connector, either within the case or one the case exterior, or an inductive current connection (e.g., 27 MHz).

Speech processor cases in accordance with the present inventions may be provided with a circuitry that works in conjunction with the speech processor 102 to augment the speech processing functionality of the BTE unit. In some instances, the case circuitry may be configured to provide the basic functions necessary for a patient to hear should the BTE speech processor cease normal functioning.

Speech processor cases in accordance with the present inventions may also include communications electronics capable of wirelessly or directly (through wire, cable, or direct electrical contact) connecting the BTE unit 100 with external devices in addition to the aforementioned headpieces and implants. Such communications electronics (e.g., an ITEL communications microchip) may be used to, for example, establish a communication link with a clinician's programming interface unit, a clinician's fitting station, and/or other external devices. Accordingly, the communication electronics may facilitate the transfer of information and/or power to and from the case and the external devices. In those instances where a cable is employed, the cable may be manually wrapped and placed within a cable receptacle within the case. Such a cable receptacle may, alternatively, include a spring-loaded reel, or equivalent structure, capable of winding and/or retracting the cable into the case.

Speech processor cases in accordance with the present inventions may be provided with an antenna coil, or equivalent structure, that that receives power through an inductive link from an external source. The power received may be used to power the operations of the case and/or charge the case's on-board power supply.

In addition the to the aforementioned volume control knob, speech processor cases in accordance with the present inventions may include exterior actuators (e.g. buttons, wheels, switches, etc.) capable of modifying various operational parameters of the BTE unit such as power, stimulation program selection, sensitivity, and other parameters. For example, a portion of the housing (e.g. the processor cover) may be provided with a rotatable wheel actuator that is physically connected to the BTE volume control knob or a button that is positioned and configured to make physical contact with a button on the BTE unit.

Speech processor cases in accordance with the present inventions may also include a display, such as a liquid crystal display, that can function as a status indicator and/or a control for the case. The display may be used to display text and/or graphics and may be accompanied by actuators or controls that permit a user to control operations of the case and/or the docked BTE unit. Such actuators or controls may also be used to prepare and send a program defining at least one set of stimulation parameters from the case to the BTE unit.

Speech processor cases in accordance with the present inventions may be provided with a wireless headpiece port that wirelessly (e.g. via radiofrequency link) connects the BTE unit to the headpiece. The wireless headpiece port, along with a headpiece connector (described above with reference to FIGS. 3-16) and a signal splitter/combiner (described above with reference to FIGS. 3-16) perform the function of establishing a communications link between the headpiece connector of a speech processor unit that is located within the speech processor storage area and a speech processor headpiece that is configured to transmit signals to an implanted cochlear stimulator and is located outside the housing, and the wireless headpiece port and a signal splitter/combiner perform the function of operably connecting the housing headpiece connector to a speech processor headpiece that is configured to transmit signals to an implanted cochlear stimulator. Accordingly, references herein to "headpiece connectors" include wireless connectors as well as connectors that require cable that runs from the case to the headpiece and the connections associated therewith included wireless and wired connections.

Speech processor cases in accordance with the present inventions may be configured to protect the BTE unit stored therein from wind, moisture, dirt, dust, and detrimental physical contact. This may be accomplished by providing watertight seals, extra padding, and/or employing hard and soft polymers as appropriate.

Speech processor cases in accordance with the present inventions may include an external, on-board microphone that picks up ambient sound pressure waves and is used in conjunction with, or instead of, the headpiece microphone 220. The case microphone may be protected from the elements (e.g., wind and water) by a wind and water resistant cover that permits sound to pass there through without substantially changing the shape of the sound waves. Such a cover may include micro-holes or be a mesh or net-type cover.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below. The inventions also include speech processor systems consisting of a speech processor unit, such as for example a BTE unit, and any of the speech processor cases described above and/or claimed below.

We claim:
1. A case, comprising:
   a housing including
      a base member,
      a speech processor storage area configured to receive a speech processor unit that has a speech processor unit headpiece connector and a user-manipulatable volume control device, a processor cover movable relative to the base member between a closed position substantially aligned with the speech processor storage area and an open position, and means for docking the speech processor unit such that the user-manipulatable volume control device faces and is covered by the processor cover when the processor cover is in the closed orientation and is not covered by the processor cover when the processor cover is in the open orientation;

a housing headpiece connector associated with the speech processor storage area and configured to be connected to the speech processor unit headpiece connector; and means for operably connecting the housing headpiece connector to a speech processor headpiece that is configured to transmit signals to an implanted cochlear stimulator.

2. A case as claimed in claim 1, wherein the speech processor unit includes a power connector, the case further comprising:

a power supply receptacle; and a power connector operably connected to the power supply receptacle, associated with the speech processor storage area, and configured to electrically connect to the speech processor power connector to the power supply receptacle.

3. A case, comprising:

a housing including
   a base member,
   a speech processor storage area configured to receive a speech processor unit that has a power connector and a user-manipulatable control device, and
   a processor cover movable relative to the base member between a closed position substantially aligned with the speech processor storage area and an open position,
   the housing being configured to dock the speech processor unit such that the user-manipulatable control device faces and is covered by the processor cover when the processor cover is in the closed orientation and is not covered by the processor cover when the processor cover is in the open orientation;

a power supply receptacle within the housing in a location other than the speech processor storage area, configured to store a power supply, and including electrical contacts; and means, associated with the speech processor storage area, for non-permanently electrically connecting the power supply receptacle electrical contacts to the speech processor unit power connector when the speech processor unit is positioned within the speech processor storage area.

4. A case as claimed in claim 3, wherein the speech processor unit includes a headpiece connector, the case further comprising:

a housing headpiece connector associated with the speech processor storage area and configured to be connected to the speech processor unit headpiece connector.

5. A case as claimed in claim 3, wherein the power supply receptacle is configured to store an electrochemical cell.

* * * * *